United States Patent [19]

Haney et al.

[11] Patent Number: 4,538,068
[45] Date of Patent: Aug. 27, 1985

[54] MANIPULATOR HAVING THERMALLY CONDUCTIVE ROTARY JOINT FOR TRANSFERRING HEAT FROM A TEST SPECIMEN

[75] Inventors: Steven J. Haney, Tracy; Richard H. Stulen; Norman F. Toly, both of Livermore, all of Calif.

[73] Assignee: The United States of America as represented by the United States Department of Energy, Washington, D.C.

[21] Appl. No.: 491,134

[22] Filed: May 3, 1983

[51] Int. Cl.³ .............................................. G01N 21/00
[52] U.S. Cl. .................... 250/443.1; 414/217
[58] Field of Search .............. 374/45, 57; 366/139, 366/142, 144; 277/81 R; 250/440.1, 443.1; 414/217

[56] References Cited

U.S. PATENT DOCUMENTS

| | | | |
|---|---|---|---|
| 2,498,479 | 2/1950 | Bensen | 277/81 |
| 2,602,899 | 7/1952 | Page | 250/440.1 |
| 2,829,261 | 4/1958 | Lowitzsch et al. | 378/208 |
| 3,214,972 | 11/1965 | Pax | 73/432 SD X |
| 3,599,475 | 8/1971 | Dubouch | 374/57 X |
| 3,909,207 | 9/1975 | Bir | 366/144 X |
| 3,969,314 | 7/1976 | Grigull | 366/139 X |
| 4,284,894 | 8/1981 | Sitte et al. | 250/443.1 |

Primary Examiner—Daniel M. Yasich
Attorney, Agent, or Firm—James H. Chafin; Albert Sopp; Judson R. Hightower

[57] ABSTRACT

A manipulator for rotatably moving a test specimen in an ultra-high vacuum chamber includes a translational unit movable in three mutually perpendicular directions. A manipulator frame is rigidly secured to the translational unit for rotatably supporting a rotary shaft. A first copper disc is rigidly secured to an end of the rotary shaft for rotary movement within the vacuum chamber. A second copper disc is supported upon the first disc. The second disc receives a cryogenic cold head and does not rotate with the first disc. A sapphire plate is interposed between the first and second discs to prevent galling of the copper material while maintaining high thermal conductivity between the first and second discs. A spring is disposed on the shaft to urge the second disc toward the first disc and compressingly engage the interposed sapphire plate. A specimen mount is secured to the first disc for rotation within the vacuum chamber. The specimen maintains high thermal conductivity with the second disc receiving the cryogenic transfer line.

16 Claims, 2 Drawing Figures

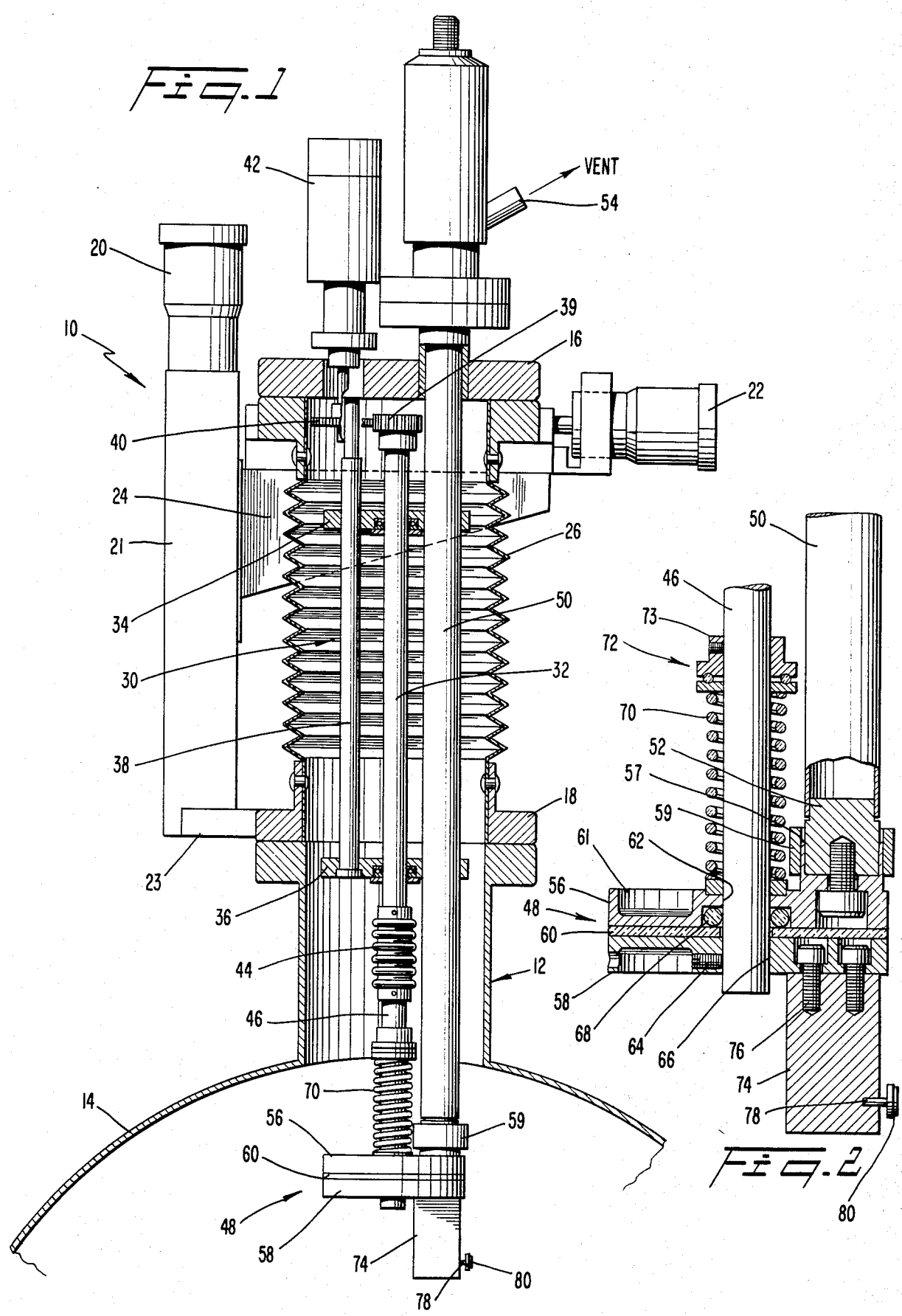

MANIPULATOR HAVING THERMALLY CONDUCTIVE ROTARY JOINT FOR TRANSFERRING HEAT FROM A TEST SPECIMEN

The U.S. Government has rights in this invention pursuant to Contract No. DE-AC04-76DP00789 between the U.S. Department of Energy and the Western Electric Company.

BACKGROUND OF THE INVENTION

The present invention relates generally to manipulators, and more particularly concerns a manipulator having a rotational mount capable of operating in ultra-high vacuum at either very high or very low temperatures. The invention will be specifically described in connection with a manipulator for cryogenically cooling a rotatable test specimen about a highly thermally conductive rotary joint movable in three mutually perpendicular directions within an ultra-high vacuum chamber.

Scientific tests and analyses of particular material specimens are best conducted at extreme temperatures under ultra-high vacuum conditions. Hence, it is necessary to conduct many of these tests in an ultra-high vacuum chamber. In many of these tests, it is highly desirable to change both the position and orientation of the test specimen within the vacuum chamber. Manipulation of the test specimen is particularly important where more than one type of surface analytical probe is utilized in the testing, as it allows the specimen to be moved to different positions for different analyses. Typical tests and analyses on material samples in this category include Auger analysis, x-ray photoelectron spectroscopy, thermal desorption spectroscopy and argon ion sputter cleaning. Furthermore, many of these tests require that the test specimen be constantly maintained at cryogenic temperature levels.

One method of maintaining a test specimen at a constant extremely low cryogenic temperature involves continuously cooling by a thermal media, such as liquid helium or liquid nitrogen. The thermal media is applied to the test specimen from a pressurized dewar through a transfer line or other piping arrangement. When the tests are performed in an ultra-high vacuum chamber, practical necessity dictates that the dewar be located outside the chamber, and that the media be piped through a sealed opening in the chamber wall. The need to seal the piping arrangement entering the ultra-high vacuum chamber conflicts with the need to supply thermal media to the test specimen when the test specimen is moved within the vacuum chamber.

A proposed arrangement for accommodating both of these conflicting needs involves supplying the thermal media to the test specimen through a relatively small (in diameter) helically wound concentric pipe arrangement. The concentric pipe arrangement is fixedly sealed as it enters the vacuum chamber. However, the discharge end of the pipe arrangement is movable within a limited range along with the test specimen. This concentric pipe arrangement resembles a helically wound spring and accommodates limited rotational movement of the test specimen. The requirement for the pipe size to be relatively small in diameter presents significant thermal conductance limitations. Moreover, this arrangement will not accommodate a full 360° of test specimen rotation.

SUMMARY OF THE INVENTION

It is thus an object of the invention to provide a manipulator capable of rotatably moving a test specimen in a vacuum chamber through a wide range of movement.

It is a further object of the invention to provide a manipulator for moving a specimen in a vacuum chamber having improved cooling capability.

It is another object of the invention to provide a manipulator for cooling a movable material specimen to cryogenic temperatures in a vacuum chamber without external frost formation.

Another object of the invention is to provide a manipulator for delivering a cryogenic media to a test specimen in an ultra-high vacuum chamber with improved efficiency.

Yet another object of the invention is to provide a manipulator with a specimen holding end portion capable of being electrically isolated from the drive mechanism.

Additional objects, advantages, and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved manipulator apparatus is provided for maintaining a rotatable material specimen at an extreme temperature. The apparatus includes a rotary shaft and a pair of relatively movable discs. A first one of the pair of discs is rigidly supported to an end of the rotary shaft and rotatable therewith, while the second disc has a centrally disposed clearance hole and is supported upon the first disc. The rotary shaft extends through the clearance hole of the second disc to the first disc. A specimen mount is secured to the first disc for rotation therewith. A plate is sandwiched between the pair of discs and serves as a bearing for facilitating relative rotary movement between the discs while maintaining heat conduction therebetween. A thermal media transfer line is secured to the second disc for cooling, and means are provided for effectuating rotary movement of the shaft whereby the specimen mount is rotated with the rotary shaft while maintaining thermal contact with the second disc cooled by the thermal media.

The discs and the interposed plate are all formed of highly thermally conductive materials. The discs are preferably formed of copper and the plate is preferably formed of sapphire.

According to a more specific aspect of the invention, a spring is disposed on the rotary shaft for urging the second disc toward the first disc to compressively engage the sapphire plate therebetween and to improve the thermal junction between the discs. The thermal media transfer line preferably directs a cryogenic fluid to the second disc to cool the sample mount through the plate and the first disc. The sample mount can be offset with respect to the axis of the rotary shaft for pronounced rotational movement, or can be on the axis depending on chamber configuration.

Preferably, spherical sapphire bearings are disposed in the second disc about the rotary shaft for facilitating rotation of the rotational shaft while electrically isolating the second disc.

More specifically, the manipulator apparatus includes a frame for supporting the rotary shaft. The frame is partially disposed in an open ended chamber adapted for sealed communication with a vacuum chamber. The frame is rigidly secured to a movable flange partially defining the open ended chamber and movable in three mutually perpendicular directions.

Still other objects of the present invention will become readily apparent to those skilled in this art from the following description wherein there is shown and described a preferred embodiment of this invention, simply by way of illustration of one of the best modes contemplated for carrying out the invention. As it will be realized, the invention is capable of other different embodiments, and its several details are capable of modifications in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification, illustrate several aspects of the present invention, and together with the description serve to explain the principles of the invention. In the drawings:

FIG. 1 is a cross sectional elevational view of a manipulator according to the present invention supporting a test specimen for rotary movement within an ultra-high vacuum chamber.

FIG. 2 is an enlarged cross sectional view of the rotary joint in the manipulator of FIG. 1.

Reference will now be made in detail to the present preferred embodiment of the invention, an example of which is illustrated in the accompanying drawings.

DETAILED DESCRIPTION OF THE INVENTION

Reference is now made to FIG. 1 illustrating a three direction translational unit 10 mounted on top of a neck 12 of an ultra-high vacuum chamber defined by the vessel 14. The translational unit is shown in a vertical orientation in the drawings and will thus be described. It should be appreciated, however, that other orientations are possible. Hence, terms such as "top", "bottom", "upper" and "lower" refer only to the illustrated orientation.

The translational unit 10 includes upper and lower support flanges 16 and 18 and three micrometer adjustments 20 and 22 (only two of which are illustrated) for moving the upper flange 16 in three mutually perpendicular directions with respect to the lower flange 18. The micrometer adjustment 20 is secured on top of a vertical support 21, which is, in turn, secured to the lower support flange 18 by a bracket 23. A vertically (as depicted) movable lifting arm 24 on the support 21 carries the upper flange 16 and effectuates relative vertical movement between the flanges 16 and 18. Micrometer adjustment 22 moves the flange 16 on a track (not illustrated) in a horizontal direction relative to the lifting arm 24, and the non-illustrated micrometer adjustment moves the flange 16 in a further horizontal direction (into and out of the plane of the illustration) on a still further track (not shown). The translational unit 10 is a commercially available component available from UHV Instruments in Burlington, Ontario, Canada. Since the details of the translational unit 10 form no past, per se, in the present invention, further description thereof will be omitted in the interest of brevity.

A flexible metal bellows 26 is welded to both the upper and lower flanges 16 and 18 to define an open ended chamber 28 in open communication with the ultra-high vacuum chamber through the neck 12. A manipulator frame 30 depends downwardly from the upper support flange 16 for supporting rotational shaft 32. The frame 30 includes upper and lower support discs 34 and 36 rigidly secured in aligned spaced relationship by a pair of columnar support members 38 (only one of which is shown in FIG. 1) formed of solid stainless steel in the preferred embodiment. The columnar support members 38 are also rigidly connected to the upper support flange 16. Hence, movement of the upper support flange 16 imparted by the translational unit 10 also moves the manipulator frame 30 relative to the ultra-high vacuum chamber 14.

The rotational shaft 32 is a 0.5 inch O.D. tube shaft in the preferred embodiment journaled in said support discs 34 and 36 by suitable bearings as shown in FIG. 1 of the drawings and extends from a position above the upper manipulator support disc 34 inside the chamber 28 to a position substantially below the lower manipulator support disc 36. A stainless steel spur gear 39 is attached to the top portion of the rotary shaft 32 in meshing relationship with a driving spur gear 40 attached to a rotary throughfeed 42.

The lower end of the rotational shaft 32 includes a formed metal bellows coupling 44 connecting the shaft 32 with an output shaft 46 supporting a rotary joint 48. The bellows coupling 44 is flexible and accommodates minor misalignment between the shafts 32 and 46.

A liquid helium or liquid nitrogen cold head 50 extends through the upper support flange 16 and the open end of the chamber 28 into the ultra-high vacuum chamber in the vessel 14. The cold head 50 also passes through the manipulator support plates 34 and 36, adding further rigidity to the frame 30. The cold head 50 is the mate for the transfer line (inside the head, not shown) providing for delivery of a cryogenic media from a pressurized dewar (not shown) to the rotary joint 48. The cryogenic media is directed down the cold head 50 for deposit onto an OFHC copper end plug 52 brazed in the bottom end of the head 50. The liquid media deposited onto the copper end plug 52 forms a gas and is vented back up the transfer line in the head 50 along two different concentric paths. The first path goes back to the dewar and precools the transfer line. The other path terminates at a vent 54 located on top of the upper support flange 16. Venting the gas produced by evaporation at a remote location and near room temperature eliminates frost formation. Liquid transfer lines of this nature are commercially available and sold under the trademark Heli-Tran.

The enlarged view of FIG. 2 more clearly illustrates the rotary joint 48. The rotary joint 48 includes upper and lower discs 56 and 58 cooperating to sandwich an interposed plate 60. The discs 56,58 and plate 60 are each formed of highly thermally conductive material; the discs 56,58 being preferably formed of copper and the plate 60 being preferably formed of sapphire. Because the parts in engagement are of dissimilar material insofar as the molecular structure is concerned, the tendency of the surfaces to bind is greatly reduced thereby minimizing the friction. The copper metal and sapphire structures are particularly suited to this function.

In the preferred embodiment, both the discs 56,58 and the sapphire plate 60 are approximately 3 inches in diameter with channels 61 milled to reduce mass. The upper disc 56 has a centrally disposed clearance hole 62 for accommodating rotary movement of the shaft 46(32). The lower disc 58 is rigidly attached to the rotary shaft 46(32) and movable therewith. In the illustrated embodiment, the lower disc 58 receives the shaft 46(32) in a centrally disposed hole 66 aligned with hole 62. A connecting pin 64 secures the lower disc 58 to the shaft 46(32).

The sapphire plate 60 has a clearance hole aligned with holes 62 and 66, and in accordance with the broad principles of the invention, serves as a bearing surface between the discs 56,58. The sapphire plate advantageously prevents galling between the relatively moving copper discs 56 and 58 while simultaneously providing excellent thermal conductivity between the discs 56,58. The thermal conductivity of the sapphire plate 60, in fact, slightly exceeds the thermal conductivity of the copper discs 56,58.

The upper disc 56 has an integral cup 57 on its upper portion for receiving the cold head 50. The cup 57 is split so that it may be radially compressed against the cold head 50 by a clamp 59 to provide good thermal contact. The interconnection between the cold head 50 and the upper disc 56 also prevents the upper disc from rotating with the rotary shaft 46(32) and the lower disc 58.

The upper disc 56 has a recess about the hole 62 for receiving the spherical sapphire bearings 68 to facilitate relative rotation of the rotary shaft 46(32). Unlike the flat bearing plate 60, the spherical bearings 68 could be replaced with hardened steel bearings. However, spherical sapphire bearings about the rotary shaft 46(32) are advantageous for many applications due to their mechanical strength and electrical insulation properties. It is desirable in many applications, for example, to electrically isolate the lower section of the manipulator. In the illustrated embodiment, this may be achieved by merely uncoupling the spur gears 39 and 40 because of the presence of the plate 60 and bearings 68.

A compression spring 70 is concentrically disposed about the rotary shaft 46(32) between the upper disc 56 and a thrust bearing assembly 72 on the rotary shaft 46(32). The spring 70 urges the upper disc 56 the lower disc 58 together to compressingly engage the interposed sapphire plate 60. The pressure exerted by spring 70 may be adjusted by sliding the mounting sleeve 73 of the bearing assembly 72 up or down on the rotational shaft 46(32). Pressure applied by the spring 70 against the upper disc 56 is important since it determines, in part, the quality of the thermal junction at the sapphire/copper disc interfaces. Improved thermal conductivity at the sapphire/copper interface occurs with increased pressure. However, the friction between the rotating discs 56 and 58 also increases with increased pressure. Thus, an optimum pressure value accommodating both of these factors is selected. Applicants have determined that a compressive force between 10 and 15 pounds to be the optimum force in the preferred embodiment. The bearing surfaces of the copper discs and sapphire plate are also finely lapped to insure optimum surface contact and enhance thermal conductivity at the sapphire/copper interfaces.

A specimen mount 74 in the form of a copper block is firmly attached to the bottom disc 58 by a plurality of screws 76. The mount 74 is preferably offset from the rotational axis of the shaft 32 for pronounced rotational movement with respect thereto.

It should be apparent, however, that other types of specimen mounts can be readily incorporated into the basic design. In effect, the manipulator of the present invention may be customized with different mounts to meet specific user needs without major modification.

In the specific embodiment illustrated, an indirect heater holding assembly 78, such as one sold by Varian Associates, Palo Alto, Calif., is clamped into the copper specimen mount 74. The illustrated heater assembly 78 is electrically powered for heating attached specimen material 80. The material specimen 80, as shown in FIG. 2, is attached to the outer face of the button-type support of the heater 78. The Varian indirect heater of the preferred embodiment is capable of raising the temperature of the specimen material to temperatures in excess of 1200° K.

It will be appreciated that the rotary joint 48 provides a thermal conduction path from the specimen 80 to the cold head 50. The application of cryogenic media to the upper disc 56 cools or extracts heat from the test specimen 80 through the upper disc 56, the plate 60, the lower disc 58 and the mount 74. By the judicious selection of the materials and the mechanical structure noted above, it has been found that the specimen 80 heated, as described may constantly be maintained at a temperature of approximately 90° K., when using liquid nitrogen as the cooling media as desired and while rotating the specimen.

In summary, numerous benefits have been described which result from employing the concepts of the invention. A manipulator capable of rotating a test specimen 360° about a rotational axis in a cryogenically cooled vacuum chamber has been provided. The manipulator includes a rotary joint for efficiently conducting heat while simultaneously allowing rotation of a test specimen. The manipulator substantially improves both the cooling capacity for a rotating specimen and increases the efficiency of a cryogenic delivery system. The preferred materials are compatible in both ultra-high vacuum and extreme temperature conditions. The preferred materials also permit the specimen holding end of the manipulator to be electrically isolated.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize in the invention in various embodiments and with various modifications as are suited to the particular use contemplated. It is intended that the scope of the invention be defined by the claims appended hereto.

We claim:

1. A manipulator for rotating a material specimen in a high vacuum environment comprising:
   a frame extending into the high vacuum environment;
   a rotary shaft carried by the frame;
   a first disc constructed of a first thermally conductive material rigidly supported by an end of the rotary shaft;

a specimen mount carried by the first disc for rotation therewith;

a second disc constructed of the first thermally-conductive material carried by the frame, said second disc being provided with a clearance hole for receiving the rotary shaft therethrough;

bearing means constructed of a second material which is thermally conductive interposed between and in contact with the first and second discs for facilitating rotary movement between the discs while maintaining thermal conduction between the discs;

means for cooling said second disc with a thermal media; and drive means for effectuating rotary movement to said rotary shaft whereby said specimen mount is rotated with said rotary shaft while maintaining a thermal conductive path from the mount through the first disc, the bearing means and the second disc.

2. A manipulator as recited in claim 1 wherein said bearing means material is also dielectric.

3. A manipulator as recited in claim 1 wherein said bearing means comprises a plate having a clearance hole therethrough for receiving the rotary shaft therethrough.

4. A manipulator as recited in claim 3 wherein said discs are formed of copper and said plate is formed of sapphire.

5. A manipulator as recited in claim 3 further including a spring disposed on said rotary shaft for urging said second disc and said first disc together and compressingly engaging the plate therebetween.

6. A manipulator as recited in claim 3 wherein said bearing means also comprises standoff bearings disposed between the second disc and the rotary shaft for facilitating rotation of the shaft with respect to the second disc.

7. A manipulator as recited in claim 6 wherein said standoff bearings are formed of sapphire for electrically isolating the second disc from the rotary shaft.

8. A manipulator as recited in claim 3 wherein said means for cooling said second disc includes a thermal media cold head connected to said second disc for directing a cryogenic fluid to the second disc to cool the specimen mount through the plate and the first disc.

9. A manipulator as recited in claim 8 further including heating means on said specimen mount for heating a specimen.

10. A manipulator as recited in claim 1 wherein said mount is offset with respect to the axis of the rotary shaft.

11. A manipulator as recited in claim 1 further including means for moving the frame in at least two mutually perpendicular directions.

12. A manipulator as recited in claim 11 wherein said frame is partially disposed in an open ended chamber adapted for sealed communication with a vacuum chamber.

13. A manipulator as recited in claim 11 wherein said frame includes first and second support discs rigidly secured in aligned relationship with each other by a plurality of columnar support members.

14. A manipulator as recited in claim 13 wherein said open ended chamber is defined by a flexible bellows extending between first and second flanges, said first flange having a central opening and being adapted for mating with a cooperating flange about an opening to a vacuum chamber and the second flange being selectively movable in at least two mutually perpendicular directions with respect to said first flange.

15. A manipulator as recited in claim 14 wherein said frame is rigidly secured to said second flange.

16. A manipulator as recited in claim 15 wherein said drive means includes a gear about the end of the rotary shaft opposite the discs and a rotary throughfeed disposed outside the open ended chamber for providing rotary power to the rotary shaft.

* * * * *